US012733618B2

(12) United States Patent
Daoust et al.

(10) Patent No.: US 12,733,618 B2
(45) Date of Patent: Sep. 15, 2026

(54) *TRAMETES VERSICOLOR* DESIGNATED AS STRAIN M2-101-03

(71) Applicant: M2 Ingredients, Inc., Vista, CA (US)

(72) Inventors: Julie Daoust, Vista, CA (US); Samuel Andrasko, Lakeside, CA (US)

(73) Assignee: M2 Ingredients, Inc., Vista, CA (US)

( * ) Notice: Subject to any disclaimer, the term of this patent is extended or adjusted under 35 U.S.C. 154(b) by 134 days.

(21) Appl. No.: 18/641,223

(22) Filed: Apr. 19, 2024

(65) Prior Publication Data

US 2024/0357989 A1 Oct. 31, 2024

Related U.S. Application Data

(60) Provisional application No. 63/636,605, filed on Apr. 19, 2024, provisional application No. 63/462,483, filed on Apr. 27, 2023.

(51) Int. Cl.
*A01H 15/00* (2006.01)
*A01G 18/20* (2018.01)
(Continued)

(52) U.S. Cl.
CPC ............. *A01H 15/00* (2013.01); *A01G 18/20* (2018.02); *A01G 18/40* (2018.02); *A23L 2/52* (2013.01); *A23L 31/00* (2016.08)

(58) Field of Classification Search
CPC ........... A01H 15/00; A23L 31/00; A23L 2/52; A01G 18/40; A01G 18/20
(Continued)

(56) References Cited

U.S. PATENT DOCUMENTS 7,001,751 B1 * 2/2006 Pfaller .................. C12N 15/52 435/6.15
2023/0279335 A1 9/2023 Gao et al.
(Continued)

FOREIGN PATENT DOCUMENTS

CN 107409743 A 12/2017
CN 114431075 A 5/2022
(Continued)

OTHER PUBLICATIONS

"Getting Into Mushroom Cultivation: Grain Spawn", Spooky Mushrooms <https://spookymushrooms.wordpress.com/2021/04/08/getting-into-mushroom-cultivation-grain-spawn/>, Apr. 8, 2021, 6 pages.
(Continued)

*Primary Examiner* — Brent T O'Hern
(74) *Attorney, Agent, or Firm* — Carr & Ferrell LLP; James M. Nachtwey

(57) ABSTRACT

Exemplary embodiments of the present disclosure may include an isolated mycelium of *Trametes versicolor* designated as strain M2-101-03. Exemplary embodiments of the present disclosure may also include a method for propagating a *Trametes versicolor* mycelium, the method including culturing a mother culture, culturing a production culture, the production culture being a sub-culture of the mother culture, creating a liquid master inoculum using the production culture, diluting the liquid master inoculum to create a diluted liquid master inoculum, creating a biomass product using the diluted liquid master inoculum, slicing the biomass product for dehydration to create a sliced biomass product, dehydrating the sliced biomass product to create a dehydrated sliced biomass product, milling the dehydrated sliced biomass product to select a designated particle size of the dehydrated sliced biomass product, and screening the des-
(Continued)

ignated particle size of the dehydrated sliced biomass product.

19 Claims, 5 Drawing Sheets
(4 of 5 Drawing Sheet(s) Filed in Color)

(51) Int. Cl.
*A01G 18/40* (2018.01)
*A23L 2/52* (2006.01)
*A23L 31/00* (2016.01)

(58) Field of Classification Search
USPC .......................................................... 426/590
See application file for complete search history.

(56) References Cited

U.S. PATENT DOCUMENTS

2024/0164424 A1* 5/2024 Andrasko ............... A23L 31/00
2024/0349663 A1* 10/2024 Andrasko .............. A01G 18/40

FOREIGN PATENT DOCUMENTS

KR 20030029423 A 4/2003
WO WO2022195581 A1 9/2022

OTHER PUBLICATIONS

"Turkey Tail Mushrooms", Spooky Mushrooms <https://spookymushrooms.wordpress.com/2021/10/27/turkey-tail-mushrooms/>, Oct. 27, 2021, 4 pages.
"Turkey tail mushroom grain spawn 3lb, mix of oats and wheat, use as spawn, substrate", Foraged, Accessed May 16, 2024 <https://www.foraged.com/products/turkey-tail-mushroom-grain-spawn-3lb-mix-of-oats-and-wheat-use-as-spawn-substrate>, 5 pages.
"Drying & Grinding Turkey Tail Mushrooms", YouTube—Pine Creek Wildlife, <https://www.youtube.com/watch?v=NmAtcd-xfLw>, Jan. 9, 2023, 2 pages.
Mirończuk-Chodakowska et al. "Beta-glucans from fungi: Biological and health-promoting potential in the COVID-19 pandemic era." Nutrients 13.11 (2021): 3960. <https://mdpi-res.com/d_attachment/nutrients/nutrients-13-03960/article_deploy/nutrients-13-03960-v2.pdf?version=1636359058>, Nov. 6, 2021, 23 pages.
"Turkey Tail Mushroom Capsules", Real Mushrooms, Accessed May 16, 2024 <https://shop.realmushrooms.com/products/organic-turkey-tail-extract-capsules>, 20 pages.
"Toniiq 30% Beta Glucans 12,000mg 10x Concentrated Ultra High Strength Turkey Tail Mushroom Extract—Highly Concentrated and Bioavailable—120 Veggie Capsules", Amazon Accessed May 16, 2024 <https://www.amazon.com/Glucans-Concentrated-Strength-Mushroom-Extract/dp/B09HJQBT3R>, 7 pages.

* cited by examiner

FIG. 4
INGREDIENTS
MYCELIAL SCIENCE
Trametes versicolor M2-101-03

FIG. 5
INGREDIENTS
MYCELIAL SCIENCE
Trametes versicolor M2-101-03

*TRAMETES VERSICOLOR* DESIGNATED AS STRAIN M2-101-03

CROSS-REFERENCE TO RELATED APPLICATION

The present U.S. Non-Provisional Patent Application claims the priority benefit of U.S. Provisional Patent Application Ser. No. 63/462,483 filed on Apr. 27, 2023, and titled "*Trametes versicolor* designated as strain M2-101-03," and the present U.S. Non-Provisional Patent Application claims the priority benefit of U.S. Provisional Patent Application Ser. No. 63/636,605 filed on Apr. 19, 2024, and titled "Systems and Methods of Liquid Submerged Fermentation for Expanding Inoculum of Fungal Species," all of which are hereby incorporated by reference in their entireties, including all patent deposit material(s) and all references cited therein.

FIELD OF THE TECHNOLOGY

Embodiments of the disclosure relate to improved strains of *Trametes versicolor* (also called Turkey tail).

BRIEF SUMMARY

Embodiments of the present disclosure include a strain of *Trametes versicolor* (also called Turkey tail) designated as strain M2-101-03 as deposited at the ATCC Patent Depository under the Budapest Treaty (10801 University Boulevard, Manassas, VA 20110), on Jul. 28, 2023, with the official deposit date of Jul. 28, 2023, and the official Patent Deposit Designation No. PTA-127611.

Embodiments of the present disclosure may include an isolated mycelium of *Trametes versicolor* designated as strain M2-101-03. In some embodiments, the isolated mycelium may be characterized by a phenotype having a distributed mass of fruitbodies on top and sides of a substrate. In some embodiments, the isolated mycelium may be characterized by a phenotype having fruiting initiation between fifteen to twenty-four days after inoculation.

Please note: all percentages cited herein are by total weight.

In some embodiments, the isolated mycelium may be characterized by a phenotype optimized to grow on oats. In some embodiments, the isolated mycelium may be characterized by a phenotype having a beta-glucan content of 20% to 35%. In some embodiments, the isolated mycelium may be characterized by a phenotype having a beta-glucan content of 25% to 35%.

In some embodiments, the isolated mycelium may be characterized by a phenotype having a beta-glucan content of 20% to 30%. In some embodiments, the isolated mycelium may be characterized by a phenotype having a beta-glucan content of 25% to 30%. In some embodiments, the isolated mycelium may be characterized by a phenotype having a beta-glucan content of 20% to 25%.

In some embodiments, the isolated mycelium may be characterized by a phenotype having a beta-glucan content of 25%. In some embodiments, the isolated mycelium may be purified. In some embodiments, the isolated mycelium may be in a powder form. In some embodiments, the isolated mycelium may be in a capsule form. In some embodiments, the isolated mycelium may be in a coffee form or other hot beverage. In yet further embodiments, the isolated mycelium may be in a form of a cold-water beverage such as a functional sports drink or protein powder.

Embodiments may also include an optimized concentration of polysaccharide peptides. Embodiments may also include an optimized concentration of polysaccharide peptides.

Embodiments of the present disclosure may also include a method for propagating a *Trametes versicolor* mycelium, the method including culturing a mother culture. Embodiments may also include culturing a production culture, the production culture being a sub-culture of the mother culture. Embodiments may also include creating a liquid master inoculum using the production culture. Embodiments may also include diluting the liquid master inoculum to create a diluted liquid master inoculum. Embodiments may also include creating a biomass product using the diluted liquid master inoculum. Embodiments may also include slicing the biomass product for dehydration to create a sliced biomass product. Embodiments may also include dehydrating the sliced biomass product to create a dehydrated sliced biomass product. Embodiments may also include milling the dehydrated sliced biomass product to select a designated particle size of the dehydrated sliced biomass product. Embodiments may also include screening the designated particle size of the dehydrated sliced biomass product.

BRIEF DESCRIPTION OF THE SEVERAL VIEWS OF THE DRAWINGS

The patent or patent application file contains at least one drawing executed in color. Copies of this patent or patent application publication with color drawing(s) will be provided by the Office upon request and payment of the necessary fee. With respect to FIGS. 2-5, the color drawings are necessary as the only practical medium by which aspects of the claimed subject matter may be accurately conveyed. The color of *Trametes versicolor* can vary. Thus, the color drawings help differentiate strain M2-101-03 as deposited at the ATCC Patent Depository under the Budapest Treaty (10801 University Boulevard, Manassas, VA 20110), on Jul. 28, 2023, with the official deposit date of Jul. 28, 2023, and the official Patent Deposit Designation No. PTA-127611 from other strains of *Trametes versicolor*. The color drawings also help differentiate a stage of growth of strain M2-101-03.

DETAILED DESCRIPTION

Figure 1:
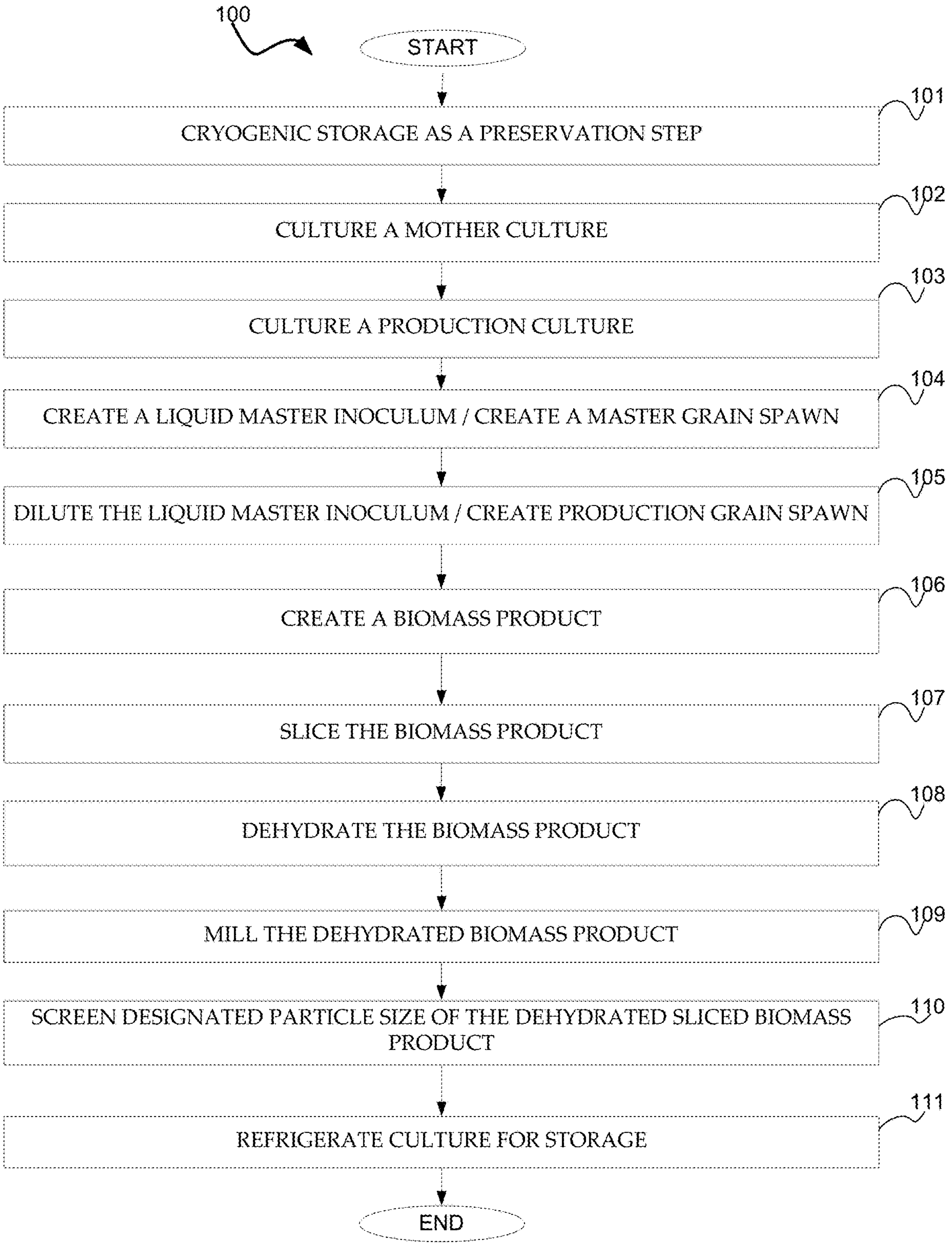
FIG. 1 is a flowchart illustrating a method for propagating a *Trametes versicolor* mycelium, according to some embodiments of the present disclosure.
Figure 2:
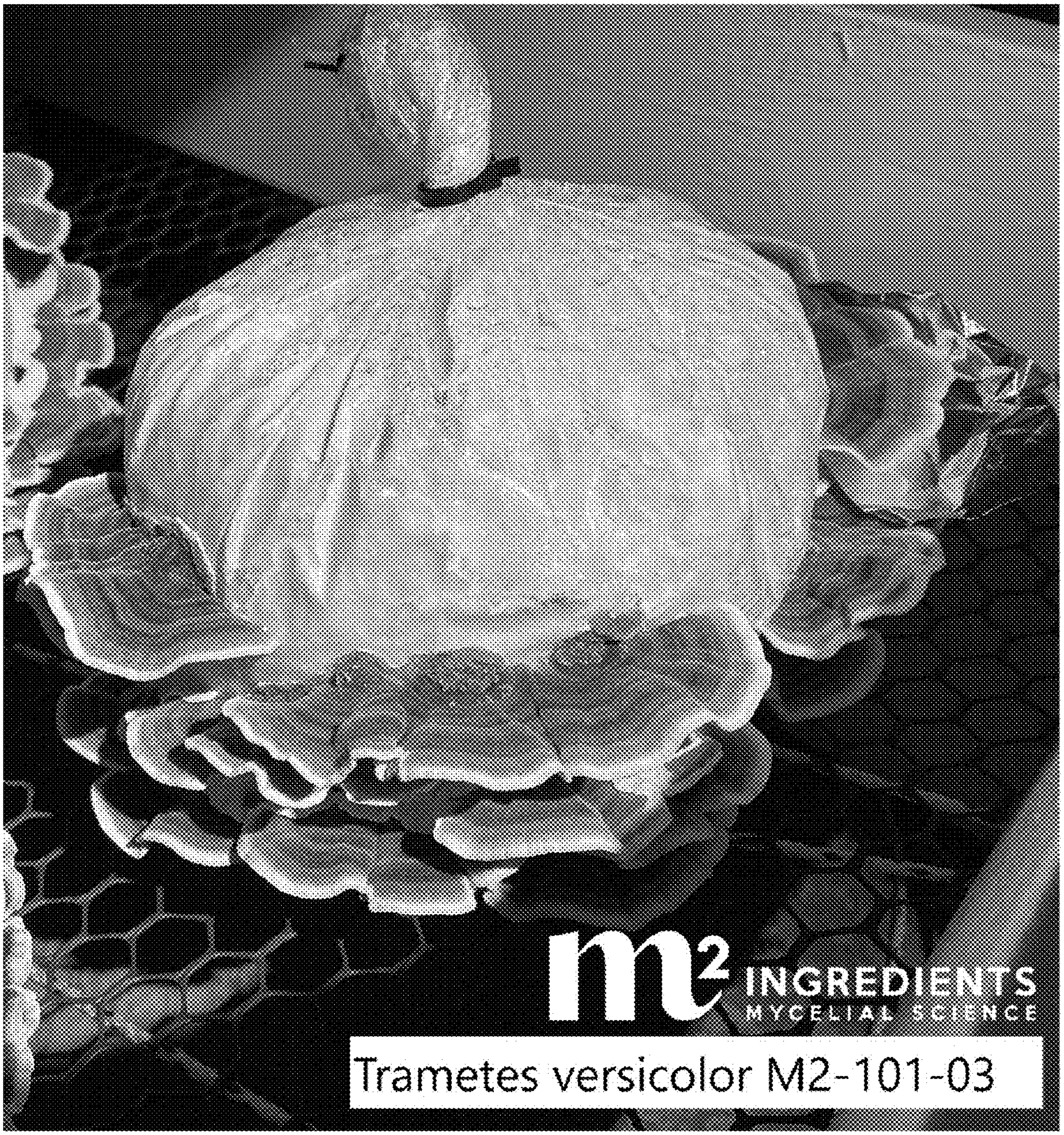
FIG. 2 is a color drawing showing a natural phenotype of *Trametes versicolor.*
Figure 3:
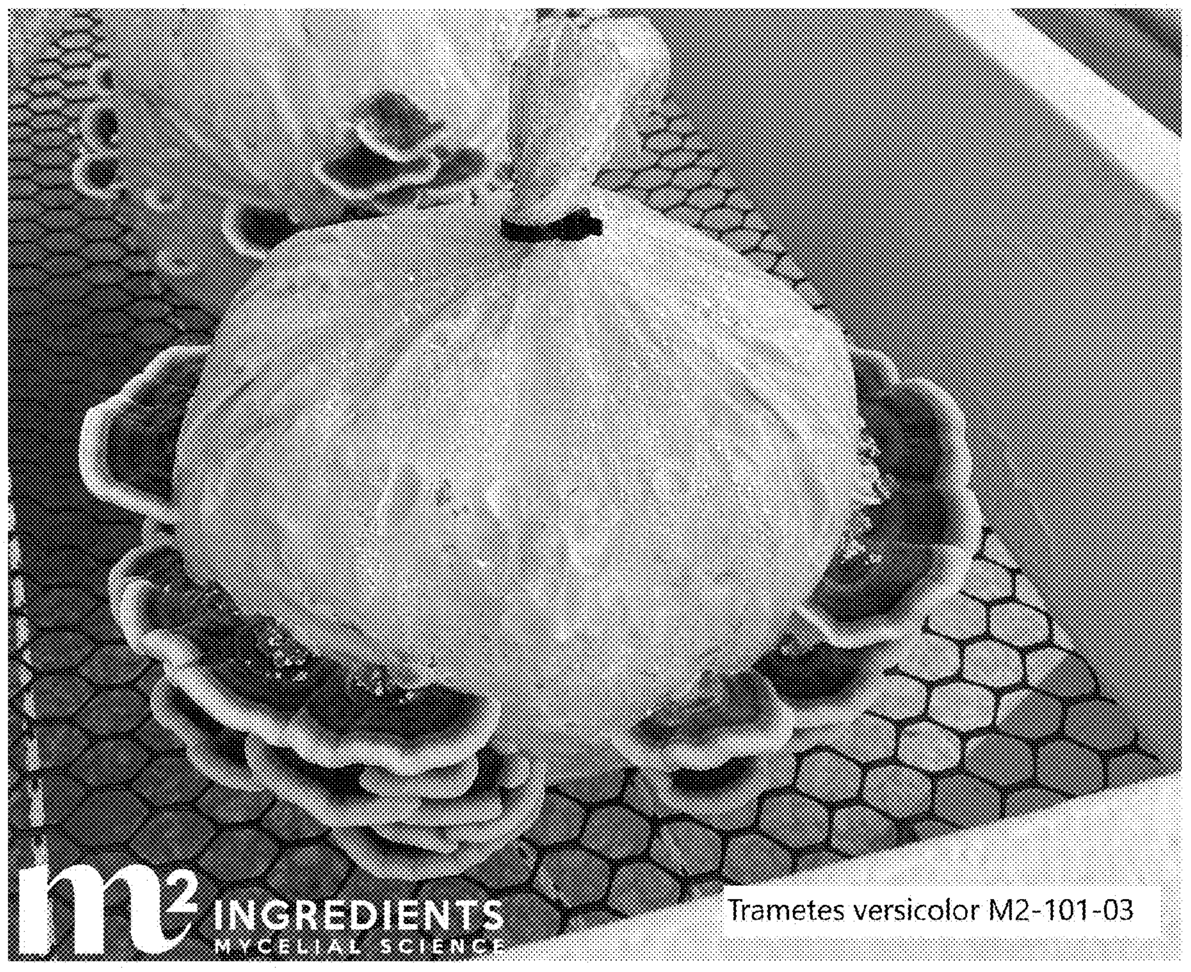
FIG. 3 is another color drawing showing a natural phenotype of *Trametes versicolor.*
Figure 4:
FIG. 4 is a color drawing showing a bioreactor bag production of *Trametes versicolor.*
Figure 5:
FIG. 5 is another color drawing showing a bioreactor bag production of *Trametes versicolor.*

*Trametes versicolor* designated as strain M2-101-03 was first cloned in a clean room after thoroughly sanitizing the outside of the selected fruitbody with ethanol. Tissue from within the fruiting body was excised and placed onto potato dextrose agar to allow the excised tissue to revert into a hyphal vegetative state. Once reverted into a hyphal vegetative state, tissue from the leading edge of the growth was transferred to chloramphenicol agar to separate the culture from bacteria that might be present in the tissue. Once the culture was shown to be free of bacteria, a section of the hypha was transferred to a new sterile PDA agar. Once the culture was purified and cleaned of any potential contaminants, the culture was transferred to oat agar comprising:

| | | |
|---|---|---|
| Agar | 10 grams | 2.00% |
| Powdered whole oat grain | 7 grams | 1.40% |
| H20 | 1 liter | |

to encourage the culture to produce the necessary enzymes needed to grow on oats and to prepare it for subsequent culturing on oats, enabling a fast transition and recovery time during subsequent transfers. The strain was grown for a period of 10 days to see a noticeable improvement in the rate of growth on oat media to ensure the necessary amylase enzymes were being produced to encourage the breakdown of starches to sugars to provide the fungus with enough energy to support the growth of the fungus.

In various embodiments, Strain M2-101-03 is grown for use in Organic Mushroom ("Om") products (Turkey tail Capsules, Turkey tail powder, Master Blend Powder, Master Blend Capsules, Mushroom Hot Chocolate, Mushroom Morning Energy), mushroom gummies and may be sold as a bulk powder under M2 Ingredients, Inc. For example, this species is used in products with immune and digestive benefits, hot beverages, drink mixes and protein powders.

In various embodiments, phenotypical characteristics of the isolated mycelium of *Trametes versicolor* designated as strain M2-101-03 includes producing a distributed mass of fruitbody on the top and sides of grain substrate. The strain, according to various exemplary embodiments, fruits best from 72-76 degrees Fahrenheit. Beta-glucan content may range from 20-35% depending on a number of days of culture before harvest. In some exemplary embodiments, the specification for this ingredient is set to a minimum of 20% beta glucans and have polysaccharide peptides at various concentration ranges.

In various embodiments, Beta-glucan concentration is 20% or greater and this specific point of at least 20% is critical or special to the operability of hot beverages and drinks. Strain M2-101-03 with a Beta-glucan concentration of 20% or greater produces a new and unexpected result, which is different in kind and not merely in degree.

In some embodiments, a grain spawn with strain M2-101-03 is specifically used for production. For example, a grain spawn is made from sterilized grains that have been inoculated with a live mycelium culture of strain M2-101-03. These inoculated grains are consumed by the growing mass of mycelium of strain M2-101-03. In various embodiments a liquid spawn of strain M2-101-03 is used as an alternative method.

FIG. 1 is a flowchart that describe a method 100 for propagating a *Trametes versicolor* mycelium, according to some exemplary embodiments of the present disclosure. At 101, cryogenic storage is used as a preservation step. At 102, the method may include culturing a mother culture. At 103, the method may include culturing a production culture on a nutrient agar comprised of a mixture of dextrose, potato starch, nutritional yeast and cauliflower powder.

In some exemplary embodiments, the mixture may comprise:

| | | |
|---|---|---|
| Dextrose | 10 grams | 2.00% |
| Potato starch | 2.5 grams | 0.50% |
| Agar | 10 grams | 2.00% |
| Cauliflower | 5 grams | 1.00% |
| Nutritional yeast | 5 grams | 1.00% |
| H20 | 1 liter | |

-continued

The cauliflower in the agar and liquid media is a source that is high in hypoxanthine which supports nucleic acid synthesis and energy metabolism in basidiomycetes. This speeds up development of the fungi. The production culture is a sub-culture of the mother culture. At 104, the method may include creating a liquid master inoculum using the production culture. At 105, the method may include diluting the liquid master inoculum to create a diluted liquid master inoculum.

In some embodiments, at 106, the method may include creating a biomass product using the diluted liquid master inoculum. At 107, the method may include slicing the biomass product for dehydration to create a sliced biomass product. At 108, the method may include dehydrating the sliced biomass product to create a dehydrated sliced biomass product. At 109, the method may include milling the dehydrated sliced biomass product to select a designated particle size of the dehydrated sliced biomass product. At 110, the method may include screening the designated particle size of the dehydrated sliced biomass product. More details according to various embodiments are disclosed below.

In some embodiments, at 102, the method may include culturing a mother culture. Fresh cultures of the *Trametes versicolor* mycelium of the M2-101-03 strain are cultured on a nutrient agar comprised of a mixture of dextrose, potato starch, nutritional yeast and cauliflower powder and grown for a period of 6-8 days until a culture diameter of 30-40 mm is obtained.

In some exemplary embodiments, the mixture may comprise:

| | | |
|---|---|---|
| Dextrose | 10 grams | 2.00% |
| Potato starch | 2.5 grams | 0.50% |
| Agar | 10 grams | 2.00% |
| Cauliflower | 5 grams | 1.00% |
| Nutritional yeast | 5 grams | 1.00% |
| H20 | 1 liter | |

5 mm×5 mm square sections of the healthiest part of the culture are cut from the leading edge of growth of the hyphae and placed into a 1.5 ml-2 ml cryogenic storage vial of 10-20 percent glycerol solution and cryogenically stored under Liquid Nitrogen (LN2). At the same time, 2 mm square sections of the same culture material are transferred to 10-20 culture tubes equal to or greater than 25 mm×150 mm in size filled with a nutrient agar comprising:

| | | |
|---|---|---|
| Dextrose | 10 grams | 2.00% |
| Potato starch | 2.5 grams | 0.50% |
| Agar | 10 grams | 2.00% |
| Nutritional yeast | 5 grams | 1.00% |
| H20 | 1 liter | |

and subsequently stored under refrigeration between 34-40 degrees Fahrenheit. Culture tubes are sub-cultured every 6-12 months to new culture tubes to verify that the cultures are still active and healthy and to preserve the phenotypic qualities of the original cultures. Cryogenic cultures previously discussed are recovered and sub-cultured into new culture tubes for storage and not used if any unwanted phenotypical variation is observed. Cryogenic culture tube is recovered by submerging the tube into a 30-degree Celsius water bath for 30 minutes and placing one agar wedge from the vial onto nutrified agar comprising:

| | | |
|---|---|---|
| Dextrose | 10 grams | 2.00% |
| Potato starch | 2.5 grams | 0.50% |
| Agar | 10 grams | 2.0% |
| Cauliflower | 5 grams | 1.00% |
| Nutritional yeast | 5 grams | 1.00% |
| H20 | 1 liter | |

Furthermore, only growth representative of the mother culture is used for inoculum.

In some embodiments at 103, the method may include culturing a production culture, the production culture being a sub-culture of the mother culture. To start the production process, mother cultures are pulled from refrigeration and sub-cultured onto 4 nutrient agar plates, each comprising:

| | | |
|---|---|---|
| Dextrose | 10 grams | 2.00% |
| Potato starch | 2.5 grams | 0.50% |
| Agar | 10 grams | 2.00% |
| Cauliflower | 5 grams | 1.00% |
| Nutritional yeast | 5 grams | 1.00% |
| H20 | 1 liter | |

Cultures are allowed to grow for 6-8 days until a growth diameter of 30-40 mm is obtained. The healthiest and most representative tissue of the mother culture is sub-cultured into step 104.

In some embodiments at 104, the method may include creating a liquid master inoculum using the production culture. Creation of master spawn is also known as "1st generation grain spawn" (G1's). An exemplary protocol is as follows: one lb. of hydrated hulled oats, hydrated to a 50-60% moisture content in a water bath at 190-195 Fahrenheit for 30 min to 60 min in a water bath is filled into an appropriate clear autoclavable bioreactor bag comprised of a polypropylene or high-density polyethylene or a polypropylene/high density polyethylene blend fitted with a microporous filter patch or strip material for gas exchange. The oats are subjected to sterilization in an autoclave for an appropriate time and temperature to fully render any present microorganisms inactive. The bags are cooled in a HEPA filtrated refrigerated cooldown room until the grain is equal to or less than 90 degrees Fahrenheit. Once cooled, the bags are delivered to a HEPA filtrated laminar flow hood and a laboratory technician subcultures a 10 mm×10 mm section of the healthiest tissue from step 105 to each individual master spawn bag. The bag is allowed to incubate at 67 degrees Fahrenheit for 7-10 days. During incubation, the bag is shaken once a 3 cm colony from around the inoculation site occurs. The bag is left to incubate until the grain is fully consolidated with the mycelium and then shaken again. The bag is then placed under refrigeration at 34-40 degrees Fahrenheit to slow down the metabolism of the culture and stall the growth. The master spawn is then monitored for contamination and regrowth every 3 days until the masters are sent to create production spawn in step 105.

In some embodiments at 105, the method may include diluting the liquid master inoculum to create a diluted liquid master inoculum.

The recipe for a primary vessel by weight

| | |
|---|---|
| Dextrose | 2.00% to 2.50% |
| Potato starch | 0.50% |
| Cauliflower | 0.25% |
| Nutritional yeast | 0.50% |

Creation of production spawn is also known as "second generation spawn" (G2's). An exemplary protocol is as follows: 7-8.5 lbs. of hydrated hulled oats, hydrated to a 40-60% moisture content in a water bath at 190-195 Fahrenheit for 30-60 min is filled into an appropriate clear autoclavable bioreactor bag comprised of a polypropylene or high-density polyethylene or a polypropylene/high density polyethylene blend fitted with a microporous filter patch or strip material for gas exchange. The oats are subjected to sterilization in an autoclave for an appropriate time and temperature to fully render any present microorganisms inactive. The bags are cooled in a HEPA filtrated refrigerated cooldown room until the grain is equal to or less than 90 degrees Fahrenheit. Once cooled, the bags are delivered to a HEPA filtrated laminar flow hood and a laboratory technician subcultures the master grain bags to the production spawn at ratio of 1:10-1:20. The production spawn bags are then incubated for 12-16 days.

In some embodiments, at 106, the method may include creating a biomass product using the diluted liquid master inoculum. An exemplary protocol is as follows: 7-8.5 lbs. of hydrated hulled oats, hydrated to a 40-60% moisture content in a water bath at 190-195 Fahrenheit for is filled into an appropriate clear autoclavable bioreactor bag comprised of a polypropylene or high density polyethylene or a polypropylene/high density polyethylene blend fitted with a microporous filter patch or strip material for gas exchange. The oats are subjected to sterilization in an autoclave for an appropriate time and temperature to fully render any present microorganisms inactive. The bags are cooled in a HEPA filtrated refrigerated cooldown room until the grain is equal to or less than 90 degrees Fahrenheit. Once cooled, the bags are delivered to a HEPA filtrated laminar flow hood and a laboratory technician subcultures the production spawn to the biomass bags at ratio of 1:180-1:200. The bags are then incubated for 50-70 days at 74 Fahrenheit-85 Fahrenheit. The bags will contain fruiting biomass, mycelium and digested oats.

In some embodiments at 107, the method may include slicing the biomass product for dehydration to create a sliced biomass product. For instance, upon harvesting the biomass, the biomass is sliced through a dicer into smaller pieces and placed upon dehydration trays for dehydration.

In some embodiments at 108, the method may include dehydrating the sliced biomass product to create a dehydrated sliced biomass product. For instance, the trays of biomass product are loaded into a static dehydrator and dried for approximately 24 hours and/or into a dynamic continuous convection belt dryer with a temperature range of 205-220 F for approximately 30 to 60 minutes to a moisture content of less than 5%. This process is carefully watched to prevent altering the taste of the final product.

In some embodiments at 109, the method may include milling the dehydrated sliced biomass product to select a designated particle size of the dehydrated sliced biomass product. For instance, the dried biomass is put though a mill and screened to a designated particle size.

In some embodiments at 110, the method may include screening the designated particle size of the dehydrated sliced biomass product. For example, the dried biomass screened to a designated particle size and bulk packed for customers. In various exemplary embodiments, the particle is screened to 60 mesh and verified through a particle analyzer.

At 111, a culture may be refrigerated for storage.

In some exemplary embodiments, air may be distributed during the incubation process across bags at a rate of 0.7 to 1.2 meters a second.

While various exemplary embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the technology as defined by the appended claims. Thus, the breadth and scope of a preferred embodiment should not be limited by any of the above-described exemplary embodiments.

What is claimed is:

1. An isolated mycelium of *Trametes versicolor* designated as strain M2-101-03 as deposited at the ATCC Patent Depository under the Budapest Treaty (10801 University Boulevard, Manassas, VA 20110), on Jul. 28, 2023, with the official deposit date of Jul. 28, 2023, and the official Patent Deposit Designation No. PTA-127611, wherein the isolated mycelium is purified.

2. The isolated mycelium of claim 1, characterized by a phenotype having a distributed mass of fruitbodies on top and sides of a substrate.

3. The isolated mycelium of claim 1, characterized by a phenotype having fruiting initiation between fifteen to twenty-four days after inoculation.

4. The isolated mycelium of claim 1, comprising amylase enzymes, the amylase enzymes breaking down starches of oat agar to sugars to enable growth of the isolated mycelium on the oat agar.

5. The isolated mycelium of claim 1, characterized by a phenotype having a beta-glucan content of 20% to 35%.

6. The isolated mycelium of claim 1, characterized by a phenotype having a beta-glucan content of 25% to 35%.

7. The isolated mycelium of claim 1, characterized by a phenotype having a beta-glucan content of 20% to 30%.

8. The isolated mycelium of claim 1, characterized by a phenotype having a beta-glucan content of 25% to 30%.

9. The isolated mycelium of claim 1, characterized by a phenotype having a beta-glucan content of 20% to 25%.

10. The isolated mycelium of claim 1, characterized by a phenotype having a beta-glucan content of 25%.

11. The isolated mycelium of claim 1, wherein the isolated mycelium is in a powder form.

12. The isolated mycelium of claim 1, wherein the isolated mycelium is in a capsule form.

13. The isolated mycelium of claim 1, wherein the isolated mycelium is in a hot beverage form.

14. The isolated mycelium of claim 1, further comprising various concentrations of polysaccharide peptides.

15. A method for propagating a *Trametes versicolor* mycelium, the method comprising:

culturing a mother culture;

culturing a production culture, the production culture being a sub-culture of the mother culture;

creating a liquid master inoculum using the production culture;

diluting the liquid master inoculum to create a diluted liquid master inoculum;

creating a biomass product using the diluted liquid master inoculum;

slicing the biomass product for dehydration to create a sliced biomass product;

dehydrating the sliced biomass product to create a dehydrated sliced biomass product;

milling the dehydrated sliced biomass product to select a designated particle size of the dehydrated sliced biomass product;

screening the designated particle size of the dehydrated sliced biomass product; and culturing the production culture onto four nutrient plates.

16. The method for propagating a *Trametes versicolor* mycelium of claim 15, the method further comprising:

culturing the mother culture on a mixture comprising approximately 10 grams of dextrose, approximately 2.5 grams of potato starch, approximately 10 grams of agar, approximately 5 grams of cauliflower, approximately 5 grams of nutritional yeast and approximately 1 liter of water.

17. The method for propagating a *Trametes versicolor* mycelium of claim 15, the method further comprising:

creating the liquid master inoculum using the production culture comprising approximately one pound of hydrated hulled oats hydrated to an approximately 50% to 60% moisture content in a water bath at approximately 190 to 195 degrees Fahrenheit for approximately 30 minutes to 60 minutes.

18. The method for propagating a *Trametes versicolor* mycelium of claim 15, the method further comprising:

screening the designated particle size of the dehydrated sliced biomass product to approximately 60 mesh.

19. An isolated mycelium of *Trametes versicolor* designated as strain M2-101-03 as deposited at the ATCC Patent Depository under the Budapest Treaty (10801 University Boulevard, Manassas, VA 20110), on Jul. 28, 2023, with the official deposit date of Jul. 28, 2023, and the official Patent Deposit Designation No. PTA-127611, further comprising various concentrations of polysaccharide peptides.

* * * * *